US010881271B2

(12) United States Patent
Aferzon et al.

(10) Patent No.: US 10,881,271 B2
(45) Date of Patent: Jan. 5, 2021

(54) ELECTRONIC ADAPTOR FOR STEREOSCOPIC FIELD OF VIEW THROUGH A PORT

(71) Applicant: AFERZON MEDICAL, LLC, Avon, CT (US)

(72) Inventors: Joshua Aferzon, Stamford, CT (US); Lee M. Nicholson, Katonah, NY (US)

(73) Assignee: Orthozon Technologies, LLC, Stamford, CT (US)

(*) Notice: Subject to any disclaimer, the term of this patent is extended or adjusted under 35 U.S.C. 154(b) by 260 days.

(21) Appl. No.: 15/794,731

(22) Filed: Oct. 26, 2017

(65) Prior Publication Data

US 2018/0116489 A1 May 3, 2018

Related U.S. Application Data

(60) Provisional application No. 62/421,564, filed on Nov. 14, 2016, provisional application No. 62/413,493, filed on Oct. 27, 2016.

(51) Int. Cl.
*A61B 1/00* (2006.01)
*A61B 1/06* (2006.01)
(Continued)

(52) U.S. Cl.
CPC ...... *A61B 1/00124* (2013.01); *A61B 1/00009* (2013.01); *A61B 1/00016* (2013.01); *A61B 1/00029* (2013.01); *A61B 1/00032* (2013.01); *A61B 1/00034* (2013.01); *A61B 1/00045* (2013.01); *A61B 1/00105* (2013.01); *A61B 1/00108* (2013.01); *A61B 1/00114* (2013.01); *A61B 1/00117* (2013.01);
(Continued)

(58) Field of Classification Search
CPC ............................ G02B 23/2415; H04N 13/02
See application file for complete search history.

(56) References Cited

U.S. PATENT DOCUMENTS

| 4,651,201 | A | 3/1987 | Schoolman |
| 5,305,121 | A | 4/1994 | Moll |

(Continued)

OTHER PUBLICATIONS

Search Report and Written Opinion issued in International Application No. PCT/US2017/058540 dated Jan. 18, 2018.

*Primary Examiner* — John P Leubecker
*Assistant Examiner* — Minqiao Huang
(74) *Attorney, Agent, or Firm* — Hoffmann & Baron, LLP

(57) ABSTRACT

An adaptor associated with a stereoscopic field of view through a port. The adaptor includes a housing, frame, and cables. The housing includes circuits associated with imaging data. The frame is connected to the housing, and has a guide and aperture. The guide extends away from the frame and is configured to pass through an opening of the port. The guide includes a terminal end configured to extend into the port such that the aperture is in communication with the opening. The cables include sensors that receive the imaging data capable of producing the stereoscopic field of view. The sensors are disposed at a distance from one another at the terminal end of the guide, wherein the distance enables the sensors to receive the image data capable of producing the stereoscopic field of view. The cables extend from the sensors of the guide to respective integrated circuits in the housing.

22 Claims, 13 Drawing Sheets

(51) Int. Cl.
  *A61B 1/04* (2006.01)
  *A61B 1/07* (2006.01)
  *A61B 1/313* (2006.01)
  *A61B 17/34* (2006.01)
  *A61B 1/32* (2006.01)
  *A61B 17/02* (2006.01)
  *A61B 90/00* (2016.01)

(52) U.S. Cl.
  CPC ...... *A61B 1/00128* (2013.01); *A61B 1/00193* (2013.01); *A61B 1/042* (2013.01); *A61B 1/0607* (2013.01); *A61B 1/0669* (2013.01); *A61B 1/07* (2013.01); *A61B 1/3132* (2013.01); *A61B 1/32* (2013.01); *A61B 17/0218* (2013.01); *A61B 17/3421* (2013.01); *A61B 17/3423* (2013.01); *A61B 2090/371* (2016.02)

(56) References Cited

U.S. PATENT DOCUMENTS

| | | | |
|---|---|---|---|
| 5,368,014 A | 11/1994 | Anapliotis et al. | |
| 6,066,090 A * | 5/2000 | Yoon | A61B 1/00045 600/113 |
| 2008/0146943 A1 * | 6/2008 | Jenkins | A61B 5/042 600/466 |
| 2008/0147018 A1 | 6/2008 | Squilla et al. | |
| 2008/0234550 A1 | 9/2008 | Hawkes et al. | |
| 2009/0318758 A1 | 12/2009 | Farr et al. | |
| 2010/0225754 A1 * | 9/2010 | Yazawa | A61B 1/00029 348/68 |
| 2010/0240961 A1 | 9/2010 | Aferzon | |
| 2010/0249512 A1 | 9/2010 | McKinley et al. | |
| 2011/0004059 A1 * | 1/2011 | Arneson | A61B 1/00041 600/109 |
| 2012/0157769 A1 * | 6/2012 | Zhu | A61B 1/00158 600/109 |
| 2014/0005484 A1 * | 1/2014 | Charles | A61B 50/13 600/201 |
| 2014/0221748 A1 * | 8/2014 | Kikuchi | A61B 1/00193 600/111 |
| 2014/0275776 A1 * | 9/2014 | Dutta | A61B 1/041 600/109 |
| 2015/0257784 A1 | 9/2015 | Corbin et al. | |
| 2016/0066850 A1 * | 3/2016 | Brockway | A61N 1/0504 600/302 |

* cited by examiner

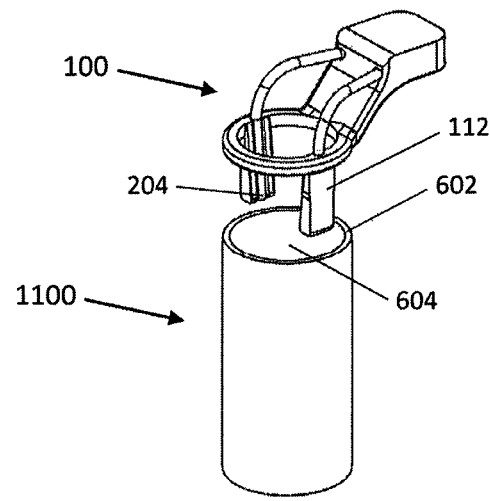
FIG. 11
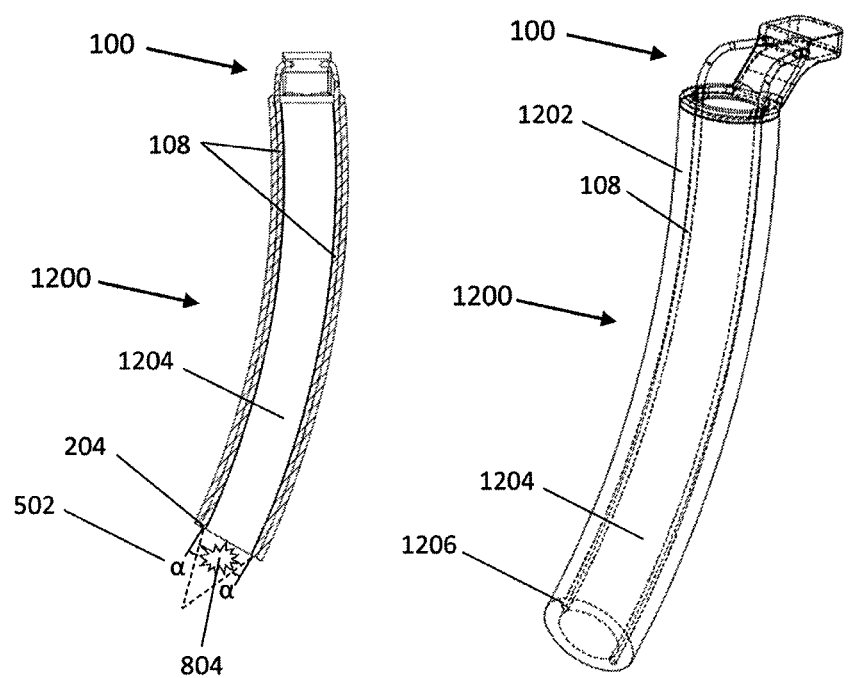
FIG. 12A     FIG. 12B

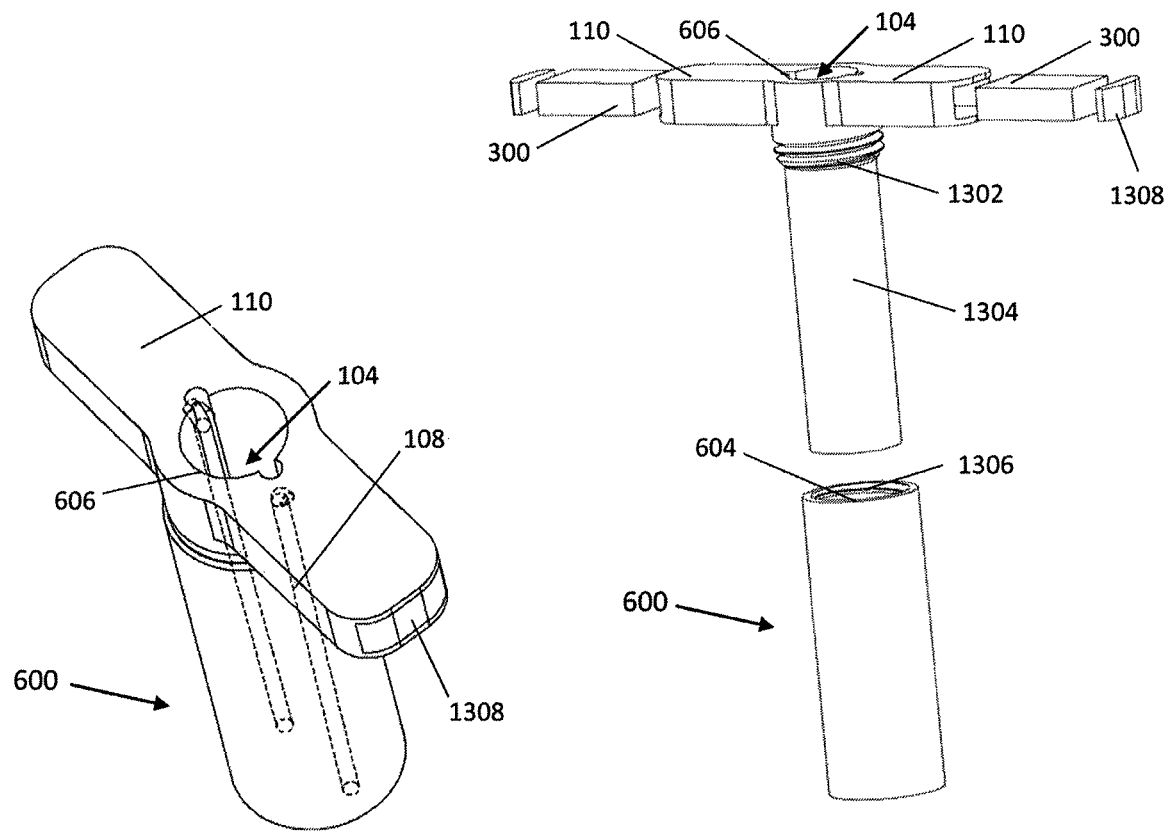
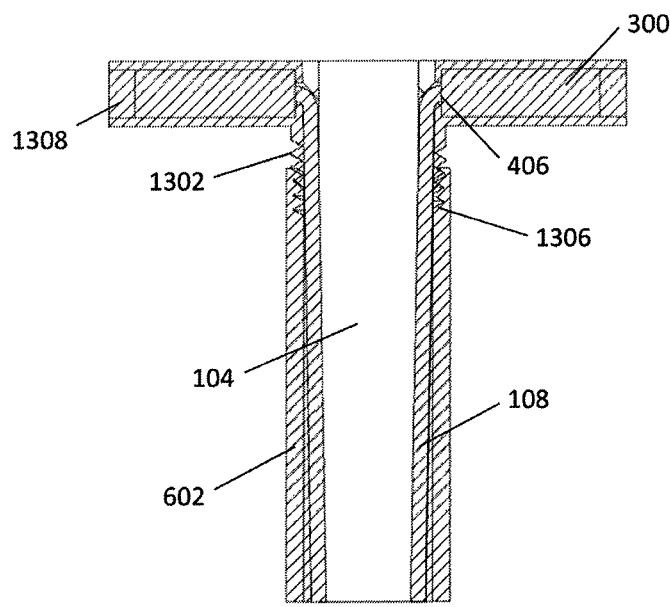
FIG. 13A  FIG. 13B
FIG. 13C

US 10,881,271 B2

ELECTRONIC ADAPTOR FOR STEREOSCOPIC FIELD OF VIEW THROUGH A PORT

CROSS REFERENCE TO RELATED APPLICATIONS

This application claims benefit of and priority to U.S. Patent Application No. 62/413,493, filed on Oct. 27, 2016, and U.S. Patent Application No. 62/421,564, filed on Nov. 14, 2016, both of which are incorporated herein by reference in their entireties.

BACKGROUND

Field

The present disclosure relates to stereoscopic visualization. More particularly, the present disclosure relates to an electronic adaptor for stereoscopic field of view through a port (e.g., retractor).

Brief Discussion of Related Art

Minimally invasive surgical techniques utilize a variety of portals, also known as ports, (e.g., retraction devices or simply retractors) to perform medical procedures through small incisions in a patient. When compared to open surgical techniques with large incisions, minimally invasive surgical techniques reduce tissue trauma, blood loss, surgical duration, probability of infection, as well as post-operative medication usage, leading to significant benefits for patients, surgeons, and hospitals.

As surgeons become more proficient with these techniques, the opening of the ports (e.g., diameter of retractors) can be reduced further to more accurately and acutely target the anatomy of the patient. However, the reduction of the opening into the patient greatly reduces a surgeon's visibility through the portal into the surgical field. The limited visibility through such reduced-opening ports spawned a variety of minimally invasive techniques for different surgical procedures that generally rely on digital image data from one or more cameras that might be disposed in relation to the surgical field.

While digital image data of conventional cameras are presented on a standalone display screen, which is typically attached to the bed side of the patient, the cameras generally deliver monoscopic data and accordingly do not enable depth perception, which might be critical in discriminating the various anatomic structures inside the patient. Moreover, the foregoing cameras are generally not designed to interact with a variety of minimally invasive ports for different surgical procedures, making the ability to deliver monoscopic digital image data to the surgeon, and especially digital image data that can be consumed by the surgeon stereoscopically (e.g., via human binocular vision), very difficult and not pragmatic for wide consumption.

More specifically, human binocular vision allows depth perception. This requires presentation of the same image data to both eyes of the human under slightly different angles. The slight difference in image projection, or parallax, to each eye can provide the surgeon's brain with relative depth information of the anatomical structures in the surgical field. In this regard, during surgery, surgeons are frequently required to interact with small, sensitive tissues and structures, such as blood vessels, nerves, ligaments, and muscles that, if injured, could result in severe patient injury or death. Current monoscopic technology does not offer surgeons depth perception, and affects negatively the ability of the surgeons to distinguish anatomical structures in the surgical field, especially where the structures are intertwined, hard-to-access, and/or poorly lit.

It is therefore desirable to provide an electronic adaptor for a stereoscopic field of view, which can be easily integrated into a variety of ports to deliver stereoscopic visualization that enables depth perception of a surgical field using a surgeon's natural binocular vision.

SUMMARY

The electronic adaptor for stereoscopic field of view through a port described herein delivers respective image data to the surgeon, enabling stereoscopic image formation in a natural binocular fashion and easily integrates into routine surgical procedures with various ports, without the associated difficulties using current technologies in connection with minimally invasive surgical procedures and associated ports.

Accordingly, there is provided an adaptor associated with a stereoscopic field of view through a port. The adaptor includes a housing, an engagement frame, and a plurality of imaging cables.

The housing includes a plurality of integrated circuits associated with a plurality of imaging data.

The engagement frame is connected to the housing, and has at least one support guide and an aperture. The at least one support guide extends away from the engagement frame and is configured to pass through an opening of the port. The at least one support guide includes at least one terminal end configured to extend at least partially into the port such that the aperture is in communication with the opening of the port.

The plurality of imaging cables includes imaging sensors that receive the plurality of imaging data capable of producing the stereoscopic field of view. The imaging sensors are disposed at a distance from one another at the at least one terminal end of the at least one support guide, wherein the distance enables the imaging sensors to receive the plurality of image data capable of producing the stereoscopic field of view. The imaging cables extend from the imaging sensors of the at least one support guide to respective integrated circuits in the housing.

The adaptor can further include a flange that extends from the engagement frame and connects the housing to the engagement frame. In some instances, the engagement frame can define a first surface and the flange can extend at an angle with respect to the first surface. The plurality of imaging cables can extend over, alongside, flush, or through the flange and engagement frame.

The at least one support guide can include a plurality of channels that receive the imaging cables, and secure the imaging sensors at the at least one terminal end.

In some embodiments, the at least one support guide can be a tubular support guide. The tubular support guide can have a first channel and a first terminal end, as well as a second channel and a second terminal end. The first channel can receive a first of the imaging cables and can secure a first of the imaging sensors at the first terminal end, while the second channel can receive a second of the imaging cables and can secure a second of the imaging sensors at the second terminal end.

The tubular support guide can include an external thread that can be configured to mate with an internal thread of the port. Moreover, the housing can include a first housing and a second housing, wherein the first housing and the second housing form a T-shape with respect to the tubular support guide of the engagement frame.

In other embodiments, the at least one support guide can include a first support guide and a second support guide. The first support guide can have a first channel and a first terminal end, while the second support guide can have a second channel and a second terminal end. The first channel can receive a first of the imaging cables and can secure a first of the imaging sensors at the first terminal end, while the second channel can receive a second of the imaging cables and can secure a second of the imaging sensors at the second terminal end.

The housing can include a light source and the imaging cables can include fiber optic bundles that transmit light from the light source to the at least one terminal end and are enabled to illuminate a field of view. The housing can also include an image transfer circuit that is connected to the integrated circuits. The image transfer circuit is configured to transfer the plurality of image data received by integrated circuits to an external processor or display.

Moreover, the housing can include a power source configured to deliver power to the integrated circuits. In various embodiments, the power source can include a battery, a radiofrequency circuit, and/or solar panel.

The radiofrequency circuit can be configured to receive radiofrequency energy from a remote source and can further be configured to convert the radiofrequency energy to power delivered to the integrated circuits. The radiofrequency circuit can also be configured to deliver power to the integrated circuits or the battery.

The solar panel can be configured to receive light energy and further can be configured to convert the light energy to power delivered to the integrated circuits. The solar panel can also be configured to deliver power to the integrated circuits or the battery.

The adaptor can also include a stabilizing attachment that is removably securable to the housing.

The stabilizing attachment can include a power source configured to deliver power to the integrated circuits. The stabilizing attachment can also include an image transfer circuit connectable to the integrated circuits, wherein the image transfer circuit can be configured to transfer the plurality of image data received by integrated circuits to an external processor or display.

The stabilizing attachment can also include a light source connectable to fiber optic bundles of the imaging cables that transmit light from the light source to the at least one terminal end and are enabled to illuminate a field of view.

BRIEF DESCRIPTION OF DRAWINGS

The accompanying drawings are presented to aid in the description of embodiments of the disclosure and are provided solely for illustration of the embodiments and not limitation thereof. Accordingly, in the drawings:

FIG. 11 illustrates an exploded view of an electronic adaptor and a second tubular port;

FIGS. 12A and 12B illustrate a perspective view and cross-sectional front view of the electronic adaptor of FIG. 1 and a third tubular port; and FIGS. 13A-13C illustrate several views of still another electronic adaptor and a fourth tubular port.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

While the various examples herein describe electronic imaging adaptors used in relation to example ports, it should be understood that the electronic imaging adaptors are not limited in their application and can thus be used in relation to various ports and retractors, whether or not related to surgical procedures.

Figure 1A:
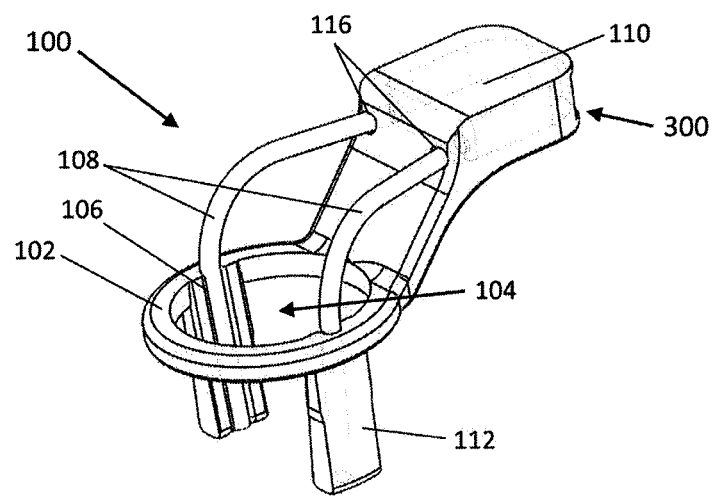
FIG. 1A illustrates a perspective view of an electronic adaptor.

FIG. 1A illustrates a perspective view of an example electronic adaptor 100. The adaptor 100 includes an adaptor housing 110 that receives an integrated electronic module 300, and an engagement frame 102 that engages a port (e.g., retractor).

The adaptor housing 110 may be made from a material such as polymer, metal, ceramic, or a composite thereof. The engagement frame 102 includes a central aperture 104, support guides 112 that extend from the central aperture 104, and channels 106 that extend along and through support guides 112.

The plurality of channels 106 support and guide the imaging cables 108 to connect with the integrated electronic module 300. While FIG. 1 depicts an embodiment where the channels 106 traverse through the support guides 112, in other embodiments one or more of the support guides 112 can omit the channels 106 and one or more of the imaging cables 108 can extend outside the support guides 112, e.g., alongside the support guides 112.

The adaptor housing 110 includes connector channels 116 that form apertures through which the connection between the integrated electronic module 300 and imaging cables 108 can be established.

Figure 1B:
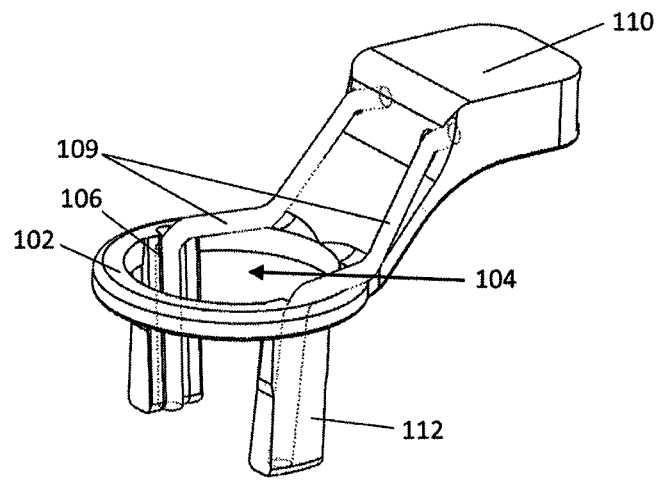
FIG. 1B illustrates a perspective view of another embodiment of an electronic adaptor.

FIG. 1B illustrates a second embodiment of an electronic adaptor 100, which includes imaging cables 109. The imaging cables 109 can extend through the adaptor housing 110 and either alongside, flush, or through the engagement frame 102 (e.g., embedded in the electronic adaptor 100) for the purposes of minimizing the profile of the imaging cables 109.

Figure 2A:
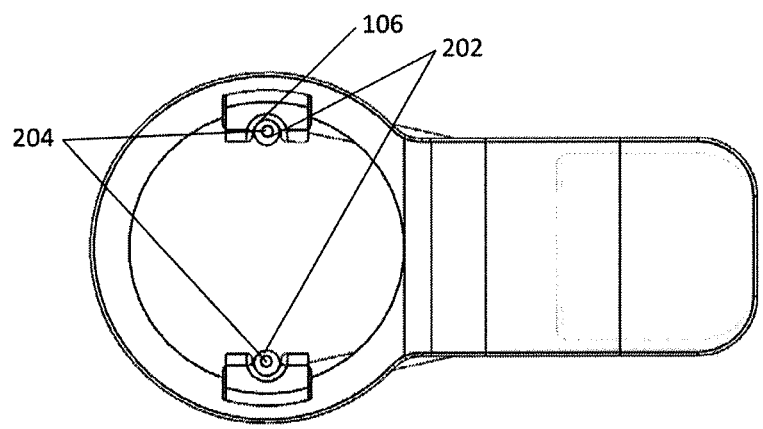
FIG. 2A illustrates a bottom view of the electronic adaptor of FIGS. 1A and 1B.

FIG. 2A illustrates a bottom view of the electronic adaptor 100, including a plurality of imaging cables 108 or 109 extending through the channels 106.

The imaging cables 108 or 109 include imaging sensors 204 that can receive and transmit images (e.g., video) to the integrated electronic module 300. The imaging cables 108 or 109 further include fiber optic bundles 202 to transmit light from the integrated electronic module 300 that can illuminate a field of view. The fiber optic bundles 202 can include a plurality of optical fibers (not shown individually).

Figure 2B:
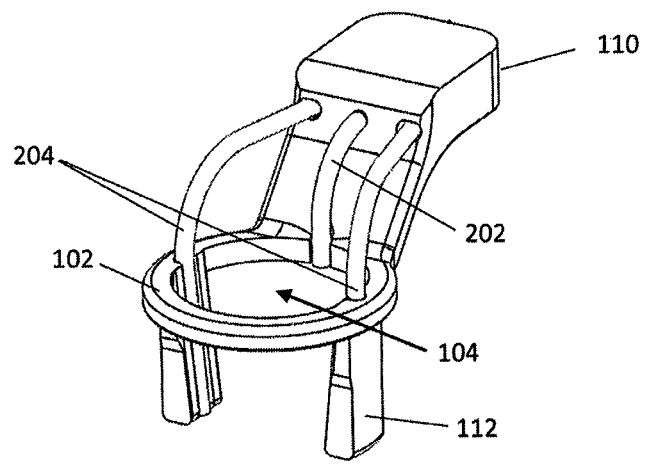
FIG. 2B illustrates a perspective view of yet another embodiment of an electronic adaptor.

FIG. 2B illustrates a perspective view of yet another embodiment of an electronic adaptor 100. In this electronic adaptor, the fiber optic bundles 202 are separate from imaging cables 108 and 109 and extend through an aperture in adaptor housing 110 into aperture 104. The fiber optic bundles 202 can include a plurality of optical fibers (not shown individually).

As illustrated in FIG. 2B, the fiber optic bundles 202 can be supported by and extend through an aperture in the engagement frame 102, and illuminate the field of view. In some embodiments, the fiber optic bundles 202 can be separated and can further extend about the engagement frame 102 and through or alongside channels 106.

Figure 3A:
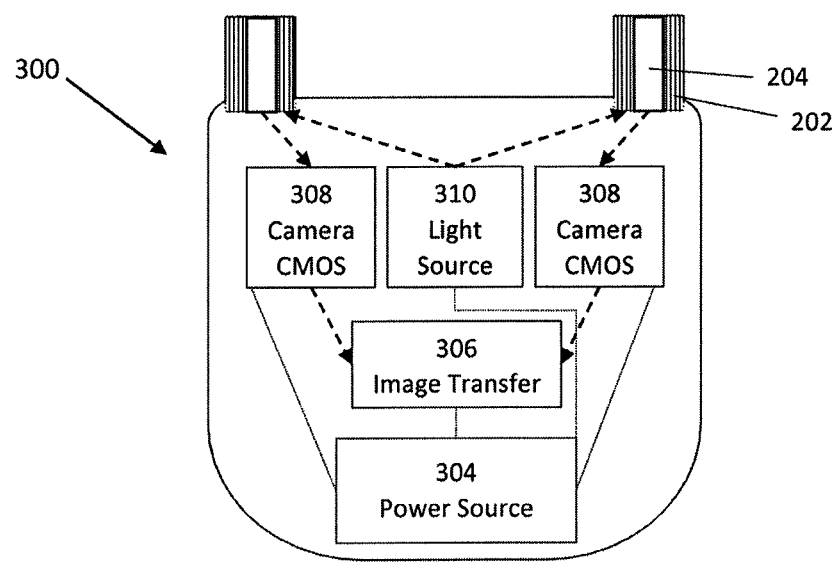
FIG. 3A illustrates a schematic view of an integrated electronic module.

FIG. 3A illustrates a schematic view of an integrated electronic module 300. The electronic module 300 includes a power source 304, a plurality of image transfer integrated circuits 306, a plurality of camera integrated circuits 308, and a light source 310. The camera integrated circuits 308 can use complementary metal oxide semiconductor (CMOS) technology.

The camera integrated circuits 308 are connected to and receive image data (e.g., video data) from the imaging sensors 204. The data is sent to and received by the image transfer integrated circuits 306. The image transfer integrated circuits 306 can transmit the received data to another processor or to an electronic display. Transmission of data can be wired or wireless.

The light source 310 delivers light energy to the fiber optic bundles 202 as illustrated in FIGS. 1A and 1B. The light source may include light-emitting diodes, one or more halogen lamps or incandescent bulbs, lasers, and/or a combination thereof. The optical fibers of the fiber optic bundles 202 transmit the energy along the imaging cables 108 or 109 to illuminate the field of view, which of course provides illumination to the imaging sensors 204.

The power source 304 delivers power to the aforementioned components of the integrated electronic module 300. The power source 304 may include a lithium-ion battery, zinc-carbon battery, alkaline battery, nickel-cadmium battery, nickel-zinc battery, nickel metal hydride battery, an electric current supply, and/or combinations thereof.

Figure 3B:
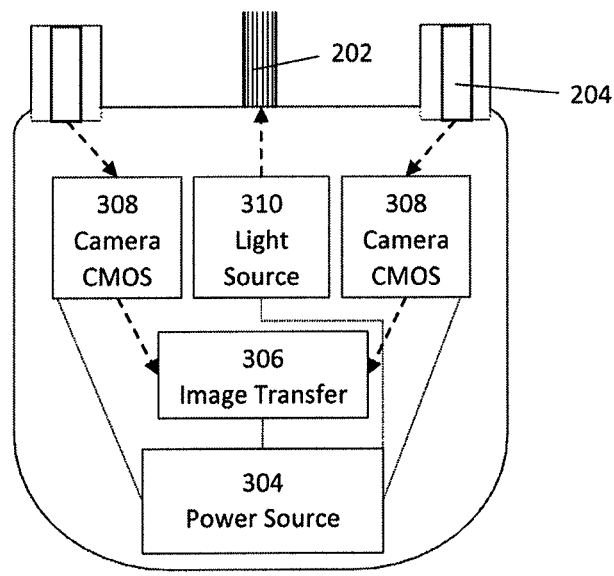
FIG. 3B illustrates a schematic view of another embodiment of an integrated electronic module.

FIG. 3B illustrates a schematic view of another embodiment of an integrated electronic module 300. The light source 310 of this integrated electronic module 300 delivers light energy to the fiber optic bundles 202 as illustrated in FIG. 2B.

Figure 3C:
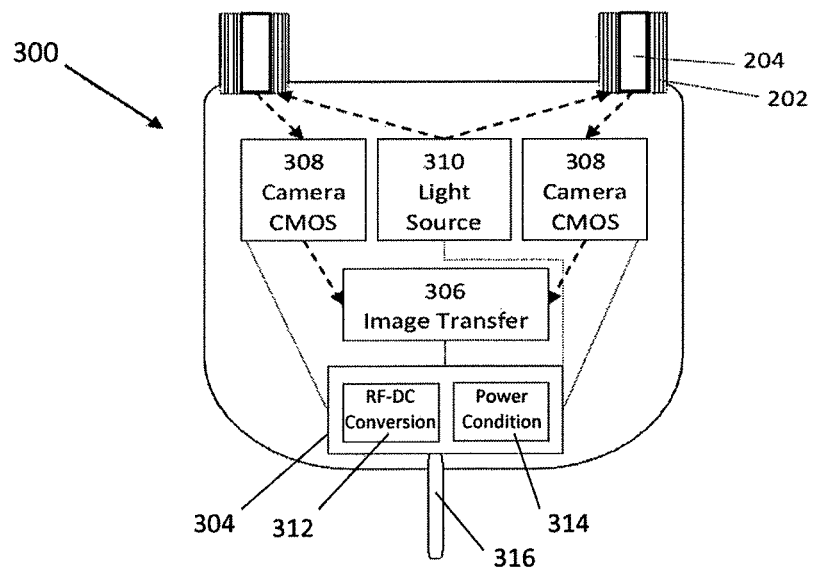
FIG. 3C illustrates a schematic view of yet another embodiment of an integrated electronic module.

FIG. 3C illustrates a schematic view of yet another embodiment of an integrated electronic module. The power source 304 delivers power to the aforementioned components of the integrated electronic module 300. As illustrated, the power source 304 includes an RF-DC conversion circuit 312, conditioning circuit 314, and an antenna 316.

The antenna 316 receives (e.g., harvests) energy (e.g., radio frequency or RF energy) from ambient radio waves, which are produced by one or more electrical appliances or sources (not shown), such as mobile telephones, handheld radios, mobile base stations, and television, radio broadcast stations, and/or any other electrical appliances capable of producing RF energy. A specifically dedicated appliance may be provided in order to supply RF energy to the integrated electronic module 300.

The conversion circuit 312 is configured to convert radio frequency (RF) energy received via the antenna 316 to direct current (DC) energy. The conditioning circuit 314 conditions the DC energy so that it could be utilized to power the aforementioned components of the integrated electronic module 300.

In some embodiments, the power source 304 can also include a battery as described with reference to FIGS. 3A and 3B. In some instances, the battery can be used (e.g., automatically) as back-up where RF energy is not received or received insufficiently to power the components of the integrated electronic module 300. In other instances, the battery may be used as described in FIGS. 3A and 3B to power the components of the integrated electronic module 300, while the circuits 312, 314 may be used to charge the battery. Supply of energy to power the components of the integrated electronic module 300 and also to charge the battery could be performed concurrently.

Figure 3D:
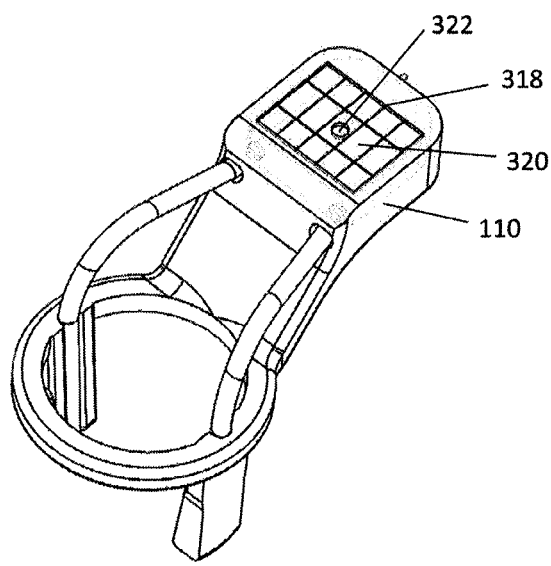
FIG. 3D illustrates a perspective view of still another embodiment of an electronic adaptor.

FIG. 3D illustrates a perspective view of still another embodiment of an electronic adaptor 100. In this electronic adaptor, the adaptor housing 110 includes a solar panel 318 configured to deliver power to the aforementioned components of the integrated electronic module 300.

The solar panel 318 is disposed atop the adaptor housing 110 so that it can receive light energy. In various embodiments, the solar panel 318 can also be disposed at different locations of the adaptor housing 110. Similarly, one or more additional solar panels can also be provided and can be disposed at different locations of the adaptor housing 110.

The solar panel 318 includes one or more solar cells 320 and an electrical connection 322. The solar cells 320 of the solar panel 318 receive light energy and further convert the light energy to direct current (DC) energy. The DC energy can be supplied to the conditioning circuit 314, which conditions the DC energy so that it could be utilized to power the aforementioned components of the integrated electronic module 300.

The electrical connection 322 is configured to connect the solar panel 318 to the power source 304 in order to deliver power to the aforementioned components of the integrated electronic module 300.

In some embodiments, the power source 304 can also include a battery as described with reference to FIGS. 3A and 3B, and/or an RF-DC device 312-316 described with reference to FIG. 3C. In some instances, the battery can be used (e.g., automatically) as back-up where light energy is not received or received insufficiently to power the components of the integrated electronic module 300. In other instances, the battery may be used as described in FIGS. 3A and 3B to power the components of the integrated electronic module 300, while the solar panel 318 may be used to charge the battery.

In still other instances, the solar panel 318 can be used in conjunction with RF-DC conversion circuit 312, whether in combination with a battery or not. More specifically, power provided by the RF-DC conversion circuit 312 and power provided by the solar panel 318 can be combined and conditioned by the conditioning circuit 314, which conditioned power can then be used as described hereinabove.

Figure 4A:
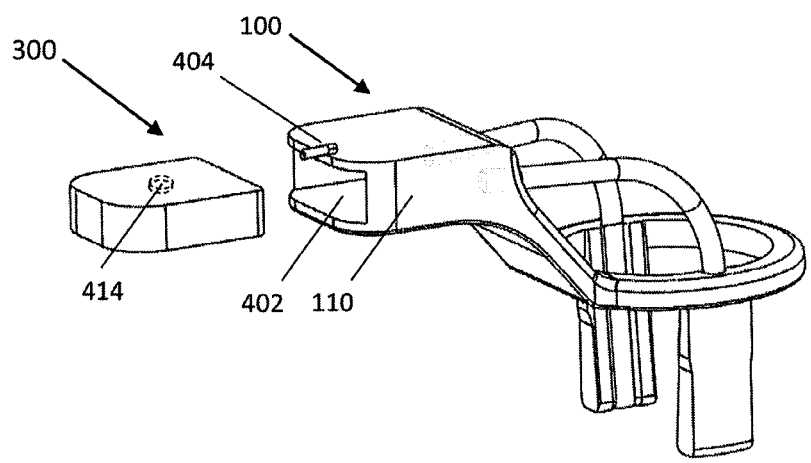
FIG. 4A illustrates an exploded perspective view of a first integrated electronic module being inserted into an adaptor housing.

FIG. 4A illustrates an exploded perspective view of a first integrated electronic module 300 being inserted into the adaptor housing 110.

The adaptor housing 110 includes an aperture 402 that can receive the first integrated electronic module 300 into the adaptor housing 110, and a locking mechanism 404 that can lock the integrated electronic module 300 in the adaptor housing 110.

The locking mechanism 404 can be rotated from its horizontal position to a vertical position over a plane of the housing aperture 402 in order to rigidly maintain the position of the integrated electronic module 300 with respect to the adaptor housing 110.

In embodiments that include a solar panel 318, or another source of power (not shown), the first integrated electronic module 300 can also include an optional electrical connection 414 that is configured to connect to the electrical connection 322 of the solar panel 318, or another source of power, when the first integrated electronic module 300 is inserted into the adaptor housing 110, in order to connect to the power source 304 that can deliver power as described herein. An example connection of the electrical connection 414 and the electrical connection 322 is described with reference to another embodiment of the electronic adaptor 100 illustrated FIG. 4F.

Figure 4B:
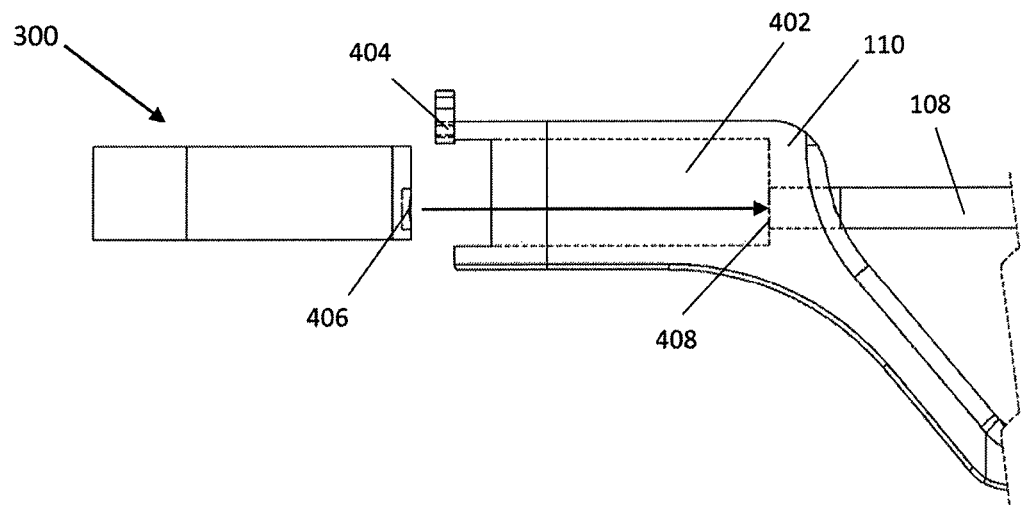
FIG. 4B illustrates an exploded side view of the first integrated electronic module being inserted into the housing aperture of the adaptor housing of FIG. 4A.

FIG. 4B illustrates an exploded side view of the first integrated electronic module 300 being inserted into the housing aperture 402 of the adaptor housing 110 of FIG. 4A.

As illustrated in FIG. 4B, the integrated electronic module 300 includes a first circuit connector 406 and the adaptor housing 110 includes a second circuit connector 408. The second circuit connector 408 can attach to the first circuit connector 406 to establish an electrical, mechanical, and/or optical connection between the integrated electronic module 300 and the imaging cables 108 or 109.

Figure 4C:
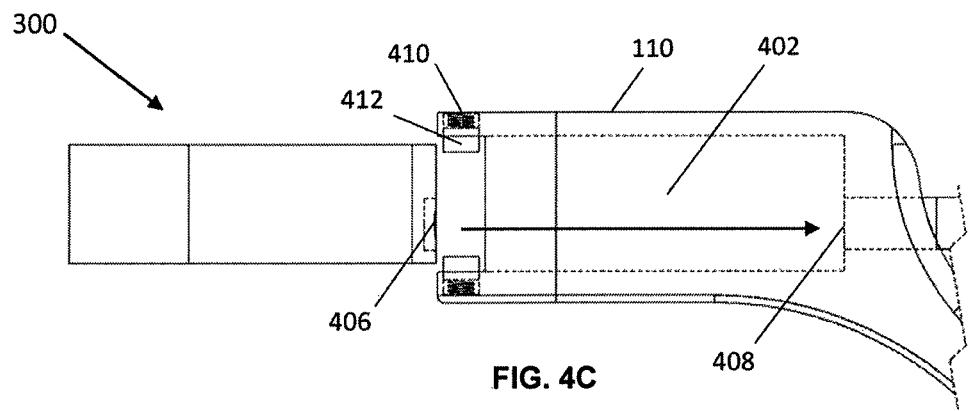
FIGS. 4C-4E illustrate insertion of the first integrated electronic module into the adaptor housing of the electronic adaptor.
Figure 4D:
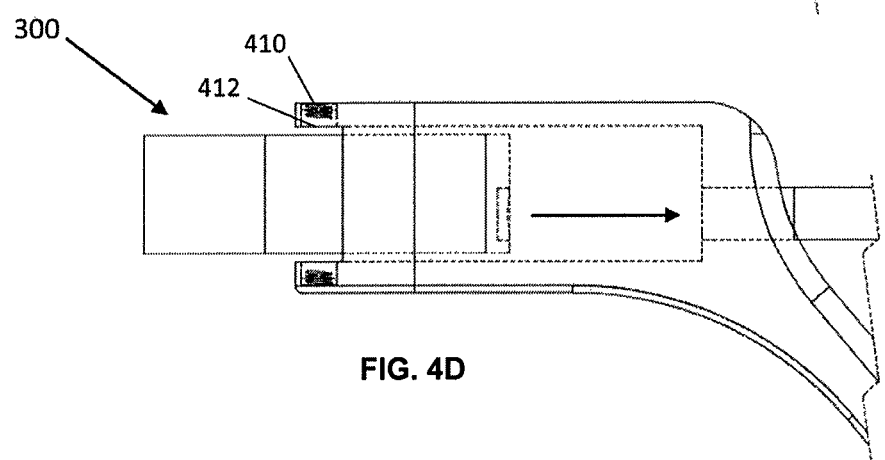
Figure 4E:
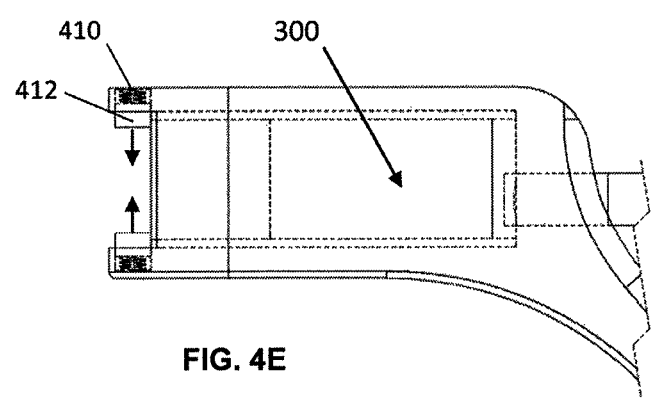

FIGS. 4C-4E illustrate a series of sequential side views of the first integrated electronic module 300 being inserted into the adaptor housing 110 of the electronic adaptor 100.

The adaptor housing 110 includes a locking mechanism which includes a snap-fit spring 410 that is attached to a snap-fit pin 412. Each of the spring 410 and pin 412 can be made out of a metal, polymer, ceramic, or composites thereof. One or more snap-fit locking mechanisms can be provided, such as one locking mechanism at the top and/or another locking mechanism at the bottom of the adaptor housing 110, as illustrated in FIGS. 4A-4E.

As illustrated in FIG. 4C, the spring 410 provides a spring mechanism that can be reduced in height from mechanical forces. The pin 412 receives mechanical forces from the first integrated electronic module 300 as it passes into the housing 110 and the pin 412 translates these forces to the spring 410. The forces reduce the height of spring 410 and reduce the height profile of the snap-fit pin 412 relative to the adaptor housing 110 thus allowing passage of the first integrated electronic module 300 into the adaptor housing 110, as illustrated in FIG. 4D.

After the first integrated electronic module 300 is positioned within the adaptor housing 110 and beyond the position of the pin 412, the spring 410 restores to its original height and the relative height profile of the pin 412, as illustrated in FIG. 4E. The pin 412 thus locks the first integrated electronic module 300 in the adaptor housing 110 and can prevent further movement of the first integrated electronic module 300 with respect to the adaptor housing 110.

Figure 4F:
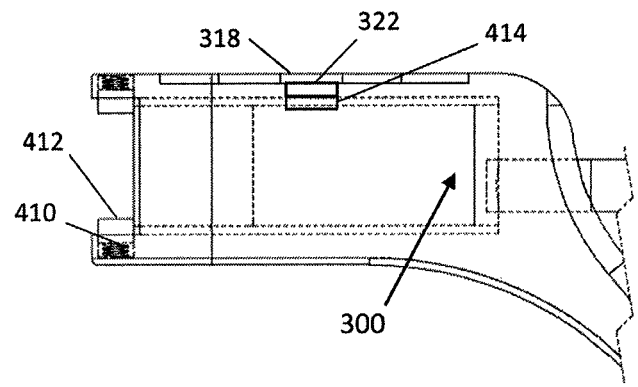
FIG. 4F illustrates the first integrated electronic module inserted into the adaptor housing of still another embodiment of an electronic adaptor.

FIG. 4F illustrates the first integrated electronic module inserted into the adaptor housing of still another embodiment of an electronic adaptor 100.

As described hereinabove with reference to FIGS. 4C-4E, when the first integrated electronic module 300 is positioned within the adaptor housing 110 and beyond the position of the pin 412, the pin 412 locks the first integrated electronic module 300 in the adaptor housing 110 and can prevent further movement of the first integrated electronic module 300 with respect to the adaptor housing 110.

In the aforementioned engagement, the electrical connection 322 of the solar panel 318, or another source of power, contacts the electrical connection 414 of the first integrated electronic module 300, which enables the solar panel 318, or another source of power, to connect to the power source 304 which can deliver power as described herein.

Figure 5:
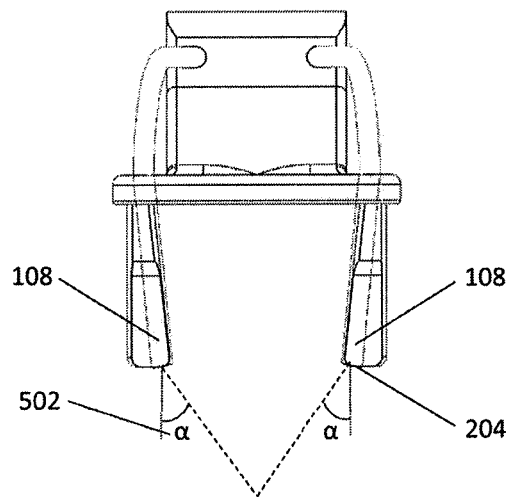
FIG. 5 illustrates a front view of the electronic adaptor of FIG. 1.

FIG. 5 illustrates a front view of an electronic imaging adaptor 100 with two imaging cables 108. The two imaging cables 108 are rigidly fixed at approximately identical and opposite parallax angles (a) 502 from a vertical trajectory that facilitate stereopsis. As a result of the parallax, the two distinct images (e.g., video streams) transmitted through the imaging cables 108 or 109 can be displayed to human pupils in order to re-create natural three-dimensional vision.

Figure 6:
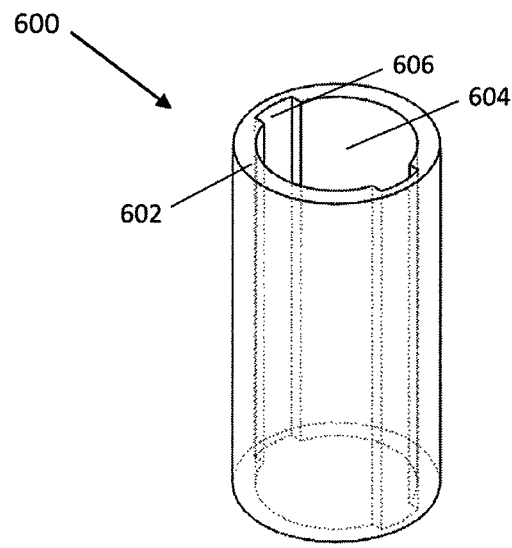
FIG. 6 illustrates a perspective view of a first tubular port.

FIG. 6 illustrates a perspective view of an example first tubular port 600. The port 600 includes a port wall 602, a central aperture 604 extending through the port wall 602, and adaptor attachments 606 that can receive and engage the support guides 112 of the electronic adaptor 100. The central aperture 604 provides an operating window through which physicians can visualize target anatomy and deliver surgical instrumentation.

Figure 7:
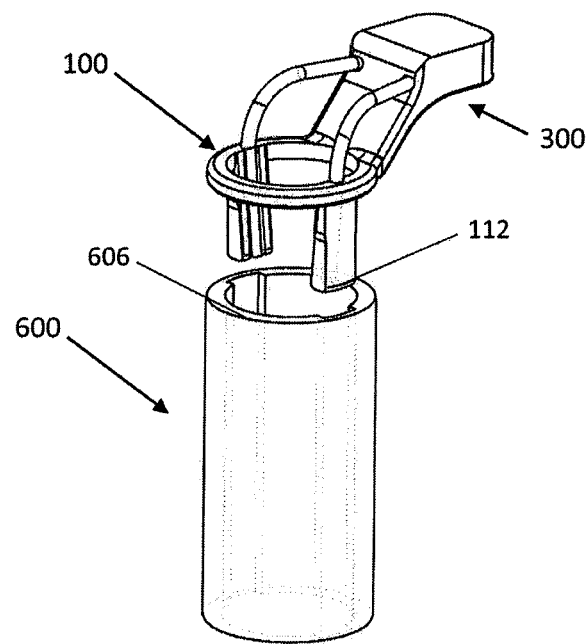
FIG. 7 illustrates an exploded view of the electronic adaptor of FIG. 1 integrating with the first tubular port of FIG. 6.

FIG. 7 illustrates a perspective view of the electronic imaging adaptor 100 being attached to the first tubular port 600.

The adaptor attachments 606 in the first tubular port 600 provide conduits through which the support guides 112 can be inserted into the port 600, and further attached to the port 600 to secure the position of the imaging cables 108 relative to the central port aperture 604.

The adaptor attachments 606 can be slots or channels cut into the wall 602 of the first tubular port 600 and can minimize the space that the support guides 112 occupy within the central aperture 604, which can maximize the surgeon's operating window. The adaptor attachments 606 allow a continuous viewing trajectory for the imaging sensors 204 down a length of the first tubular port 600.

Figure 8A:
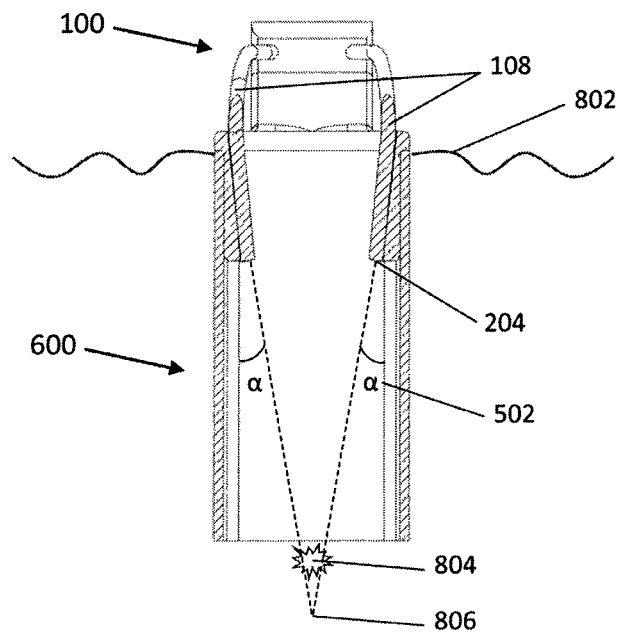
FIG. 8A illustrates a cross-sectional front view of the electronic adaptor integrated with the first tubular port of FIG. 7.

FIG. 8A illustrates a cross-sectional front view of the electronic adaptor 100 attached to the first tubular port 600.

As illustrated in FIG. 8A, the first tubular port 600 is inserted through a layer 802 (e.g., skin layer) that creates an operating window into subcutaneous anatomy of a patient. The electronic adaptor 100 includes two imaging cables 108 that are rigidly fixed at respective parallax angles (a) 502. The field of view of the imaging sensors 204 included in the imaging cables 108 or 109 intersect at a focal point 806.

An example object-of-interest 804 is shown to be located between the imaging sensors 204 and the focal point 806. The imaging sensors 204 generate two distinct images (e.g., video feeds) of the object-of-interest 804 that can be displayed stereoscopically. The skin layer 802 is described as a skin layer of a human or animal. However, in alternate embodiments the layer 804 may be a liquid, metal, polymer, ceramic, air, and/or composites thereof. In such cases, the first tubular port 600 could be used to visualize structures of various target objects.

Figure 8B:
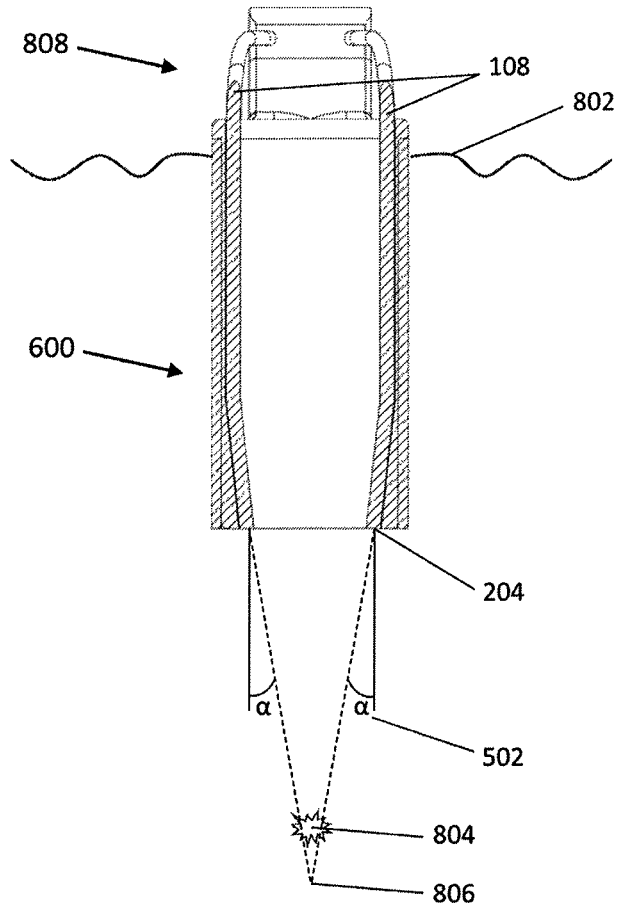
FIG. 8B illustrates a cross-sectional front view of a second electronic adaptor integrated with the first tubular port of FIG. 6.

FIG. 8B illustrates a cross-sectional front view of a second electronic adaptor 808 attached to the first tubular port 600. For example, the first tubular port 600 is inserted through the skin layer 802 and creates an operating window into subcutaneous anatomy of a patient.

As illustrated in FIG. 8B, the second electronic adaptor 808 has two imaging cables 108 or 109 that are rigidly fixed at respective parallax angles (a) 502 approximately at a terminal end of the first tubular port 600. The fields of view of the imaging sensors 204 intersect at the focal point 806, which is deeper than in FIG. 8A.

The object-of-interest 804 is located between the imaging sensors 204 and the focal point 806. The imaging sensors 204 provide two distinct images of the object-of-interest 804 that can be displayed stereoscopically. The length of imaging cables 108 or 109 are longer compared to the imaging cables 108 or 109 of the electronic adaptor 100 and illustrates how the focal point can be varied depending on the relative location of the imaging sensors 204 to the layer 802. It should be noted that the field of view of the imaging sensors 204 is not limited by the port wall 602 and can thus capture more image data to the periphery of the wall 602 of the first tubular port 600.

Figure 9:
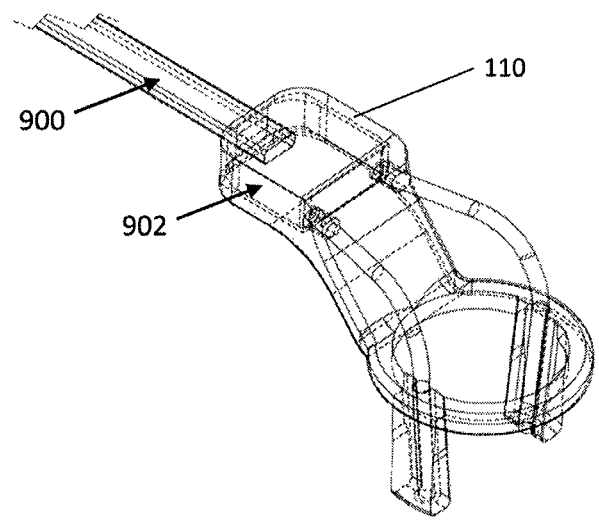
FIG. 9 illustrates a perspective view of an adaptor housing, an externally-powered integrated electronic module, and a stabilizing attachment.

FIG. 9 illustrates a perspective view of adaptor housing 110.

The adaptor housing 110 includes an externally-powered integrated electronic module 902. The externally-powered integrated electronic module 902 is connected to a stabilizing attachment 900 that rigidly secures position of the adaptor housing 110 to the stabilizing attachment 900 and also provides power to the externally-powered integrated electronic module 902.

Figure 10A:
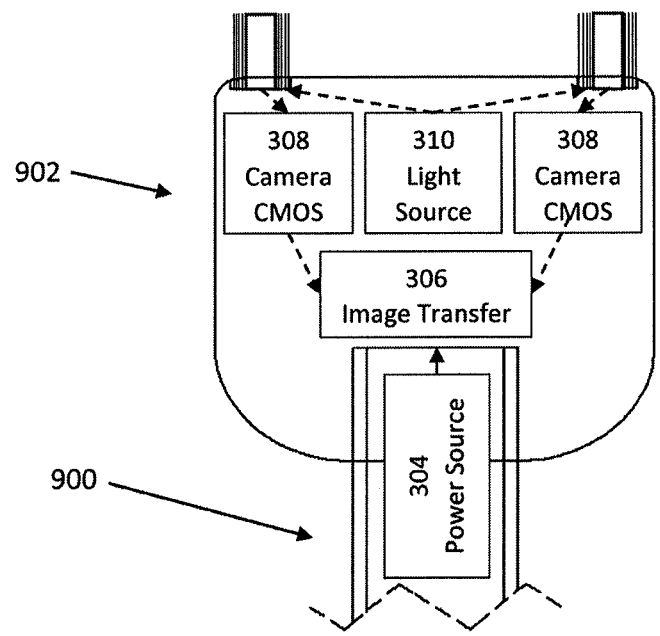
FIG. 10A illustrates a schematic view of the externally-powered integrated electronic module of FIG. 9.

FIG. 10A illustrates a schematic view of a second integrated electronic module 902 connected to a stabilizing attachment 900.

The second integrated electronic module 902 includes a plurality of image transfer integrated circuits 306, a plurality of camera integrated circuits 308, and a light source 310.

The camera integrated circuits 308 are connected to and receive image data (e.g., video data) from the imaging sensors 204. This data is sent to and received by the image transfer integrated circuits 306. The image transfer integrated circuits 306 can transmit the data to another processor or to an electronic display.

The light source 310 delivers light energy to the fiber optic bundles 202. The stabilizing attachment 900 includes a power source 304 that, when connected, can deliver power to the second integrated electronic module 902. The power source 304 may be made from a lithium-ion battery, zinc-carbon battery, alkaline battery, nickel-cadmium battery, nickel-zinc battery, nickel metal hydride battery, an electric current supply, and/or some combinations thereof.

While the current embodiment illustrates the power source 304 being located proximally to a tip of the stabilizing attachment 900 illustrated in FIG. 10A, the power source 304 may be located farther along the stabilizing attachment 900, and therein deliver power through electrically-conductive cables that can run from the power source 304 to the tip of the stabilizing attachment 900.

Figure 10B:
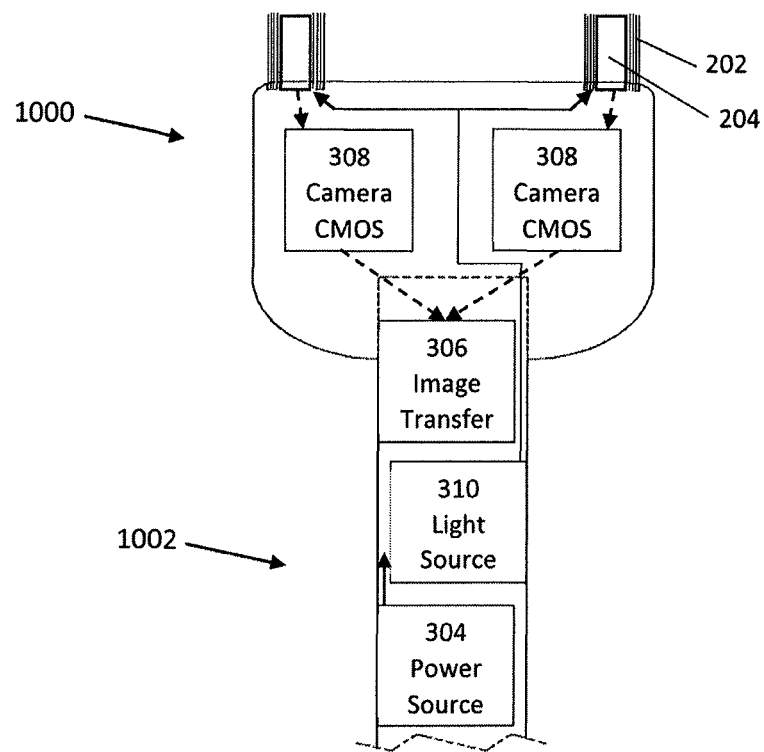
FIG. 10B illustrates a schematic view of another embodiment of an externally-powered integrated electronic module.

FIG. 10B illustrates a schematic view of a third integrated electronic module 1000 connected to a second stabilizing attachment 1002. The third integrated electronic module 1000 includes as a plurality of camera integrated circuits 308 that connect to and receive image data (e.g., video data) from the imaging sensors 204.

The second stabilizing attachment 1002 includes a power source 304, a plurality of image transfer integrated circuits 306, and a light source 310. The power source 304 delivers power to all components of the system and may be made from a lithium-ion battery, zinc-carbon battery, alkaline battery, nickel-cadmium battery, nickel-zinc battery, nickel metal hydride battery, an electric current supply, and/or combination thereof.

The image transfer integrated circuits 306 receive image data from the camera integrated circuits 308. The data can thus be transmitted from the image transfer integrated circuits 306 to another processor or to an electronic display.

The light source 310 delivers light energy to the fiber optic bundles 202. The light source 310 may include light-emitting diodes, one or more halogen lamps or incandescent bulbs, lasers, and/or combinations thereof.

Figure 10C:
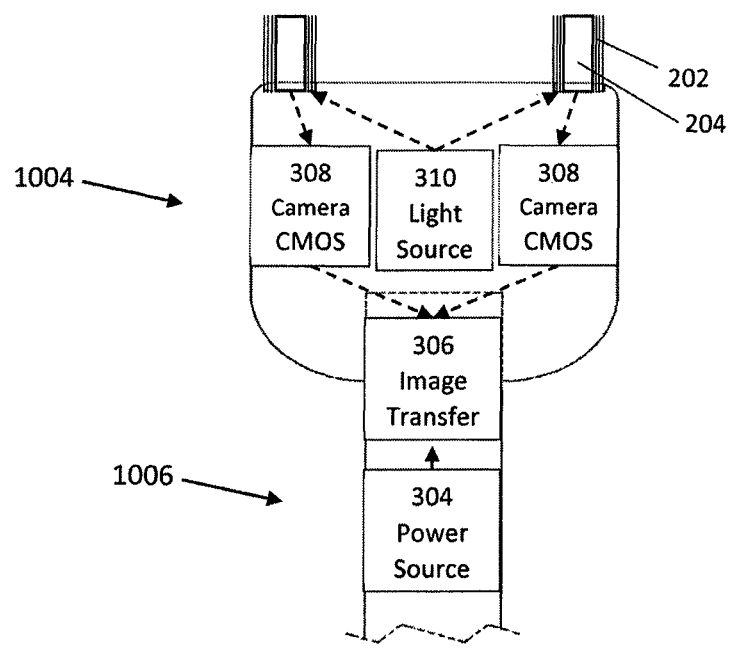
FIG. 10C illustrates a schematic view of yet another embodiment of an externally-powered integrated electronic module.

FIG. 10C illustrates a schematic view of a fourth integrated electronic module 1004 connected to a third stabilizing attachment 1006.

The fourth integrated electronic module 1004 includes as a plurality of camera integrated circuits 308 that connect to and receive image data (e.g., video data) from the imaging sensors 204, and a light source 310.

The light source 310 delivers light energy to the fiber optic bundles 202. The light source 310 may include light-emitting diodes, one or more halogen lamps or incandescent bulbs, lasers, and/or combinations thereof.

The third stabilizing attachment 1006 includes a power source 304 and a plurality of image transfer integrated circuits 306. The power source 304 delivers power to all components of the system and may be made from a lithium-ion battery, zinc-carbon battery, alkaline battery, nickel-cadmium battery, nickel-zinc battery, nickel metal hydride battery, an electric current supply, and/or combinations thereof.

The image transfer integrated circuits 306 receive image data (e.g., video data) from the camera integrated circuits 308. The data can thus be transmitted from the image transfer integrated circuits 306 to another processor or to an electronic display.

FIG. 11 illustrates an exploded view of the electronic imaging adaptor 100 and an example second tubular port (e.g., retractor) 1100. The second tubular port 1100 includes a port wall 602 and a central aperture 604 extending through the port wall 602. The support guides 112 are sized and dimensioned such that they can fit within a diameter of the central aperture 604 and provide a continuous viewing trajectory for the imaging sensors 204 along the length of the second tubular port 1100.

FIGS. 12A and 12B illustrate perspective views of an electronic imaging adaptor 100 and a third tubular port (e.g., retractor) 1200. The third tubular port 1200 includes a third tubular port wall 1202, a third tubular central port aperture 1204, and third tubular adaptor channels 1206 that extend along the length of the third tubular port wall 1202.

The third tubular port wall 1202 has at least one curvature along its length, and may have rigid or flexible physical characteristics. The imaging cables 108 or 109 of the electronic imaging adaptor 100 can be either embedded in the third tubular port wall 1202, or can extend through the third tubular adaptor channels 1206.

As illustrated in FIGS. 12A and 12B, the imaging cables 108 can exit near the end of the third tubular port wall 1202 and can provide an open trajectory for the imaging sensors 204 to visualize objects-of-interest 804 near or beyond the end of the third tubular port 1200.

FIGS. 13A-13C illustrate several views of still another electronic adaptor 100 and a fourth tubular port (e.g., retractor) 600. FIG. 13A illustrates the electronic adaptor 100 engaged with the fourth tubular port 600, while FIG. 13B illustrates components of the electronic adaptor 100 and the fourth tubular port 600 that facilitate engagement. FIG. 13C illustrates a cross-section of FIG. 13A.

The adaptor 100 includes several adaptor housings 110 that extend about the aperture 104, which can be equidistantly spaced to form a T-handle. The T-handle can be used to screw the electronic adaptor 100 into engagement with the port 600 via respective external/internal threading 1302, 1306, as illustrated in FIG. 13B. The support guide (e.g., tubular wall) 1304 of the adaptor 100 can extend or telescope with respect to the aperture 604 of port 600 such that the adaptor 100 can be inserted and threaded into the port 600.

As described herein, each of the adaptor housings 110 receives an integrated electronic module 300, which can be any of the examples as provided herein. Each adaptor housing 110 includes components for a respective imaging cable 108 or 109. For example, the first adaptor housings 110 houses camera integrated circuit 308, light source 310, image transfer 306, and power source 304 for a first imaging cable 108 or 109, and a second opposing adaptor housing 110 houses camera integrated circuit 308, light source 310, image transfer 306, and power source 304 for a second imaging cable 108 or 109.

In some embodiments, some or all of the light source 310, image transfer 306, and power source 304 for both imaging cables 108 or 109 can be located in the first or the second opposing adaptor housings 110, and can communicate with both imaging cables 108 or 109.

The imaging cables 108 from the respective adaptor housings 110 extend through the adaptor attachments 606, which extend along the tubular wall 1304. The adaptor attachments 606 can be slots or channels that are cut into the tubular wall 1304 of the electronic adaptor 100.

The plurality of adaptor attachments 606 support and guide the cables 108 to connect with the respective integrated electronic modules 300.

Accordingly, an electronic adaptor associated with a stereoscopic field of view through a port has been described. As described herein, the electronic adaptor can be integrated with cameras, lighting, and image transmission capabilities, which can facilitate a stereoscopic field of view through a port. Moreover, the electronic adaptor can be integrated with various surgical ports (e.g., retractors) and can capture video through the ports, enabling generation of the stereoscopic field of view.

Although specific example embodiments or aspects have been described, it will be evident that various modifications and changes may be made to these embodiments or aspects without departing from the broader scope of the invention. Thus, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects illustrated. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 CFR § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus, the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be claimed and which can also be incorporated into the Detailed Description.

What is claimed is:

1. An adaptor removably connectable to a retractor and associated with capturing a stereoscopic field of view through the retractor, the adaptor comprising:

a housing including a plurality of integrated circuits associated with a plurality of image data;

an engagement frame connected to the housing, the engagement frame having a top surface, at least one support guide, and an aperture extending through the top surface and having an inner periphery, the at least one support guide intersecting the top surface at the inner periphery of the aperture and extending away from the engagement frame, the at least one support guide configured to pass through an opening of the retractor as the adapter is being connected to the retractor, the at least one support guide including at least one terminal end configured to extend at least partially into the retractor such that the aperture is in communication with the opening of the retractor when the adaptor is connected to the retractor; and a plurality of imaging cables including imaging sensors that receive the plurality of image data capable of producing the stereoscopic field of view, the imaging sensors disposed at a distance from one another at the at least one terminal end of the at least one support guide disposed at least partially in the retractor, the imaging cables extending from the imaging sensors of the at least one support guide to respective integrated circuits in the housing, the distance enabling the imaging sensors to receive the plurality of image data through the retractor, the plurality of image data capable of producing the stereoscopic field of view.

2. The adaptor according to claim 1, further comprising a flange that extends from the engagement frame, the flange connecting the housing to the engagement frame.

3. The adaptor according to claim 2, wherein the plurality of imaging cables extend over, alongside, flush, or through the flange and engagement frame.

4. The adaptor according to claim 2, wherein the engagement frame defines a first surface, wherein the flange extends at an angle with respect to the first surface.

5. The adaptor according to claim 1, wherein the plurality of imaging cables extend over, alongside, flush, or through a flange and engagement frame.

6. The adaptor according to claim 1, wherein the at least one support guide comprises a plurality of channels that receive the imaging cables, and secure the imaging sensors at the at least one terminal end.

7. The adaptor according to claim 1, wherein the at least one support guide is a tubular support guide, the tubular support guide having a first channel and a first terminal end, and a second channel and a second terminal end, wherein the first channel receives a first of the imaging cables and secures a first of the imaging sensors at the first terminal end, and the second channel receives a second of the imaging cables and secures a second of the imaging sensors at the second terminal end.

8. The adaptor according to claim 7, wherein the tubular support guide includes an external thread that is configured to mate with an internal thread of the retractor.

9. The adaptor according to claim 8, wherein the housing includes a first housing and a second housing, the first housing and the second housing forming a T-shape with respect to the tubular support guide of the engagement frame.

10. The adaptor according to claim 1, wherein the at least one support guide comprises a first support guide and a second support guide, the first support guide having a first channel and a first terminal end, the second support guide having a second channel and a second terminal end, wherein the first channel receives a first of the imaging cables and secures a first of the imaging sensors at the first terminal end, and the second channel receives a second of the imaging cables and secures a second of the imaging sensors at the second terminal end.

11. The adaptor according to claim 1, wherein the housing includes a light source and the imaging cables include fiber optic bundles that transmit light from the light source to the at least one terminal end and are enabled to illuminate a field of view.

12. The adaptor according to claim 1, wherein the housing includes an image transfer circuit connected to the integrated circuits, the image transfer circuit configured to transfer the plurality of image data received by integrated circuits to an external processor or display.

13. The adaptor according to claim 1, wherein the housing includes a power source configured to deliver power to the integrated circuits.

14. The adaptor according to claim 13, wherein the power source is a battery.

15. The adaptor according to claim 13, wherein the power source includes a radiofrequency circuit configured to receive radiofrequency energy from a remote source and further configured to convert the radiofrequency energy to power delivered to the integrated circuits.

16. The adaptor according to claim 15, wherein the power source includes a battery, the radiofrequency circuit configured to deliver power to the integrated circuits or the battery.

17. The adaptor according to claim 13, wherein the power source is includes a solar panel configured to receive light energy and further configured to convert the light energy to power delivered to the integrated circuits.

18. The adaptor according to claim 17, wherein the power source includes a battery, the solar panel configured to deliver power to the integrated circuits or the battery.

19. The adaptor according to claim 1, further comprising a stabilizing attachment that is removably securable to the housing.

20. The adaptor according to claim 19, wherein the stabilizing attachment includes a power source configured to deliver power to the integrated circuits.

21. The adaptor according to claim 19, wherein the stabilizing attachment includes an image transfer circuit connectable to the integrated circuits, the image transfer circuit configured to transfer the plurality of image data received by integrated circuits to an external processor or display.

22. The adaptor according to claim 19, wherein the stabilizing attachment includes a light source connectable to fiber optic bundles of the imaging cables that transmit light from the light source to the at least one terminal end and are enabled to illuminate a field of view.

* * * * *